US012692495B2

(12) United States Patent
Gronke et al.

(10) Patent No.: US 12,692,495 B2
(45) Date of Patent: Jul. 28, 2026

(54) METHODS OF PREPARING OLIGONUCLEOTIDE COMPOSITIONS USING ULTRAFILTRATION/DIAFILTRATION

(71) Applicant: BIOGEN MA INC., Cambridge, MA (US)

(72) Inventors: Robert S. Gronke, Cambridge, MA (US); Jonas P. Immel-Brown, Cambridge, MA (US); Geetha Govindan, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 1011 days.

(21) Appl. No.: 17/801,196

(22) PCT Filed: Feb. 19, 2021

(86) PCT No.: PCT/US2021/018856
§ 371 (c)(1),
(2) Date: Aug. 19, 2022

(87) PCT Pub. No.: WO2021/168306
PCT Pub. Date: Aug. 26, 2021

(65) Prior Publication Data
US 2023/0116671 A1 Apr. 13, 2023

Related U.S. Application Data

(60) Provisional application No. 62/979,687, filed on Feb. 21, 2020.

(51) Int. Cl.
*C12N 15/113* (2010.01)
*C12N 15/10* (2006.01)

(52) U.S. Cl.
CPC ........ *C12N 15/113* (2013.01); *C12N 15/1017* (2013.01); *C12N 2310/11* (2013.01); *C12N 2310/313* (2013.01)

(58) Field of Classification Search
CPC .............. C12N 15/113; C12N 15/1017; C12N 2310/11; C12N 2310/313
See application file for complete search history.

(56) References Cited

U.S. PATENT DOCUMENTS

| | | |
|---|---|---|
| 2002/0096474 A1 | 7/2002 | Colman |
| 2009/0275088 A1 | 11/2009 | Templeton |
| 2010/0105124 A1 | 4/2010 | Pham et al. |
| 2010/0273254 A1 | 10/2010 | Budahazi et al. |

FOREIGN PATENT DOCUMENTS

| | | |
|---|---|---|
| WO | 2008/006899 A1 | 1/2008 |
| WO | 2012/010711 A1 | 1/2012 |
| WO | 2012/040184 A2 | 3/2012 |
| WO | 2014/140211 A1 | 9/2014 |
| WO | 2014/152966 A1 | 9/2014 |
| WO | 2016/193206 A1 | 12/2016 |
| WO | 2019/023439 A1 | 1/2019 |
| WO | 2020/234632 A1 | 11/2020 |

OTHER PUBLICATIONS

Andrews, B. I., et al. J. Org. Chem. 2021, 86, 49-61. (Year: 2021).*
I. Cedillo, B. Jarvis, and T. Pavone, "Designing Commercial-Scale Oligonucleotide Synthesis," Pharmaceutical Technology 44 (2) 2020. (Year: 2020).*
Latulippe et al., Salt-induced changes in plasmid DNA transmission through ultrafiltration membranes. Biotechnology and Bioengineering. Feb. 1, 2008;99(2):390-398.
Li et al., Enhanced purification of plasmid DNA isoforms by exploiting ionic strength effects during ultrafiltration. Biotechnology and Bioengineering. Sep. 29, 2015;113(4):783-9.
Hoffmann et al., RNA aptamers and spiegelmers: synthesis, purification, and post-synthetic PEG conjugation. Curr Protoc Nucleic Acid Chem. Sep. 2011;Chapter 4:Unit 4.46.1-30.
International Search Report and Written Opinion for Application No. PCT/US2021/018856, dated Jun. 14, 2021, 14 pages.

* cited by examiner

*Primary Examiner* — Andrea Olson
*Assistant Examiner* — Samuel L Galster
(74) *Attorney, Agent, or Firm* — McCarter & English, LLP; Xin Zhang; Zhongyu "Alex" Wang

(57) ABSTRACT

Disclosed herein are methods for preparing compositions containing oligonucleotides. Methods of this disclosure involve subjecting an aqueous solution of a oligonucleotide to ultrafiltration/diafiltration (UF/DF) in order to form a retentate containing the oligonucleotide, where the ultrafiltration/diafiltration (UF/DF) is carried out using an aqueous buffer solution containing one or more salts. Also disclosed herein are oligonucleotide-containing compositions obtained by these methods.

22 Claims, 12 Drawing Sheets

Drop in Permeate Flux During Buffer Exchange

Permeate Flux (L*m-2*hr-1)

Diavolumes

—●— 50 mM Ammonium Acetate     —⊘—100 mM Ammonium Acetate

—⊘— 200 mM Ammonium Acetate

DF Buffer Effect on Second Steady State Permeate Flux $y = 0.6528x - 1.174$
$R^2 = 0.9965$ DF Buffer Conductivity (mS/cm)

Permeate Flux at Second Steady State
($L*m^{-2}*hr^{-1}$)

Maximum ASO Concentration in the Retentate

Post-Lyo Trends for Sodium and Ammonium Content $y = 0.0602x + 0.0212$ $y = -0.0485x + 4.6314$ % NaOAc vs NH4OAc in UF Buffer ● Sodium    ◉ Ammonium % mass Na Content Post-UF/DF

Lyophilizer Chamber with LyoGuard Trays

Lyophilized Material in the Tray & Bag

UF/DF Concentration of Alpha Syn into RODI

Lyophilized API Platform Process Final Steps

Ethanol Precipitation
- ≤ 15% ethanol
- 100 mg/mL
- Na+ content 5.2% ± 0.9%

Lyophilization
- Na+ content 5.2% ± 0.9%
- <0.80% acetate

Compounding
- Bioburden filtration
- Reconstitution

Aqueous-Based Platform Process Final Steps

AEX
- 700 mM NaCl
- 2-4 mg/mL

UF/DF
- 150 mM NaCl
- 20 mg/mL
- 12-16 LMH Flux

DS
- Ready-to-fill DS

FIG. 12

METHODS OF PREPARING OLIGONUCLEOTIDE COMPOSITIONS USING ULTRAFILTRATION/DIAFILTRATION

CROSS REFERENCE TO RELATED APPLICATIONS

This application is a 35 U.S.C. § 371 national stage filing of International Application No. PCT/US2021/018856, filed on Feb. 19, 2021, which claims the benefit of the filing date, under 35 U.S.C. § 119(e), of U.S. Provisional Application No. 62/979,687, filed on Feb. 21, 2020, the entire contents of which are incorporated herein by reference.

FIELD OF THE DISCLOSURE

This application relates to biopharmaceutical technology in general and more specifically to methods for preparing high-purity oligonucleotide compositions using filtration techniques capable of controlling the content of salts in the oligonucleotide compositions. Methods of this disclosure successfully link the use of ultrafiltration/diafiltration (UF/DF) with lyophilization, in a manner that avoids the need to perform additional processing steps that are generally used in the production of lyophilized (solid) active pharmaceutical ingredients (APIs).

BACKGROUND

Oligonucleotides are short DNA or RNA oligomers that can be chemically synthesized for research and medical purposes. Oligonucleotides are typically prepared by a stepwise addition of nucleotide residues to produce a specific sequence. Following completion of the synthesis of the oligonucleotide in the desired sequence, the target oligonucleotide is typically obtained as a mixture along with failed sequences and other process and product related impurities.

Preparation of oligonucleotides for therapeutic use, such as commercial oligonucleotides approved for use by the FDA, is further complicated by stringent commercial specifications and drug product validation requirements. Suitable purification and formulation techniques for therapeutic oligonucleotides must take into account the chemical composition and stability of the product, as well as the mode of administration.

Therapeutic oligonucleotides are typically prepared using either an aqueous-based platform process or a lyophilized API platform process, depending on the form of the drug product required. A lyophilized (solid) drug product is potentially preferable to a liquid drug product for some products based on stability profiles, ease of storage, and ease of processing.

Spinraza® (nusinersen) is an antisense oligonucleotide (ASO) drug used for treating spinal muscular atrophy (SMA), a rare neuromuscular disorder. Commercial Spinraza® drug product is a lyophilized API derived from a solvent-intensive process. There is a need to integrate an aqueous based platform process, which ends in a liquid drug substance produced via ultrafiltration/diafiltration (UF/DF), with a lyophilized API that has specified salt (e.g., sodium and acetate) content. This approach would minimize drug product validation and meet existing commercial specifications without the need to add any non-platform liquid volume reduction steps and/or equipment.

SUMMARY OF THE DISCLOSURE

This disclosure describes methods of using ultrafiltration/diafiltration (UF/DF) to concentrate and buffer exchange oligonucleotides, in order to obtain aqueous oligonucleotide solutions that are suitable for lyophilization without additional (intervening) processing steps. FIG. 1 illustrates how methods of this disclosure are capable of integrating an aqueous-based platform process using UF/DF with a lyophilized API platform process, in a manner that eliminates the need to perform the solvent-based precipitation that generally precedes the lyophilization step.

In particular, the methods disclosed herein are capable of controlling pre- and post-lyophilization sodium contents as well as post-lyophilization acetate content in the oligonucleotide API to meet pre-determined sodium and acetate specifications. This is achieved by controlling the components (e.g., salts) in the UF/DF aqueous buffer solution. The methods described herein are also capable of controlling the membrane permeate flux and the retentate concentration of the oligonucleotide while performing the UF/DF step within manufacturer recommended conditions of transmembrane pressure (TMP).

One aspect of the present disclosure relates to a method for preparing a composition comprising an oligonucleotide, wherein the method comprises subjecting an aqueous solution of the oligonucleotide to ultrafiltration/diafiltration (UF/DF) to form a retentate comprising the oligonucleotide, and wherein the ultrafiltration/diafiltration (UF/DF) is carried out using an aqueous buffer solution comprising one or more salts.

Another aspect of the present disclosure relates to compositions comprising an oligonucleotide, wherein the compositions are obtained by one of the methods described herein.

In some embodiments, the composition is in the form of an aqueous solution comprising the oligonucleotide.

In some embodiments, the composition is in the form of a lyophilized composition comprising the oligonucleotide.

Additional objects, advantages and other features of the present disclosure will be set forth in part in the description that follows and in part will become apparent to those having ordinary skill in the art upon examination of the following or may be learned from the practice of the present disclosure. The advantages of the present disclosure may be realized and obtained as particularly pointed out in the appended claims. As will be realized, the present disclosure is capable of other and different embodiments, and its several details are capable of modifications in various obvious respects, all without departing from the present disclosure. In this regard, the description herein is to be understood as illustrative in nature, and not as restrictive.

BRIEF DESCRIPTION OF DRAWINGS

FIG. 12 illustrates how sodium ($Na^+$) ions and ammonium ($NH_4^+$) ions may occupy different counterion positions along a negatively charged phosphorothioate oligonucleotide backbone.

DETAILED DESCRIPTION

Disclosed herein are methods that integrate the use of ultrafiltration/diafiltration (UF/DF) into a lyophilized API platform process that is traditionally used to prepare solid form of oligonucleotide active pharmaceutical ingredients (APIs). Embodiments of this disclosure include methods for preparing oligonucleotides for therapeutic use, such as antisense oligonucleotide Spinraza® (nusinersen).

Figure 11:
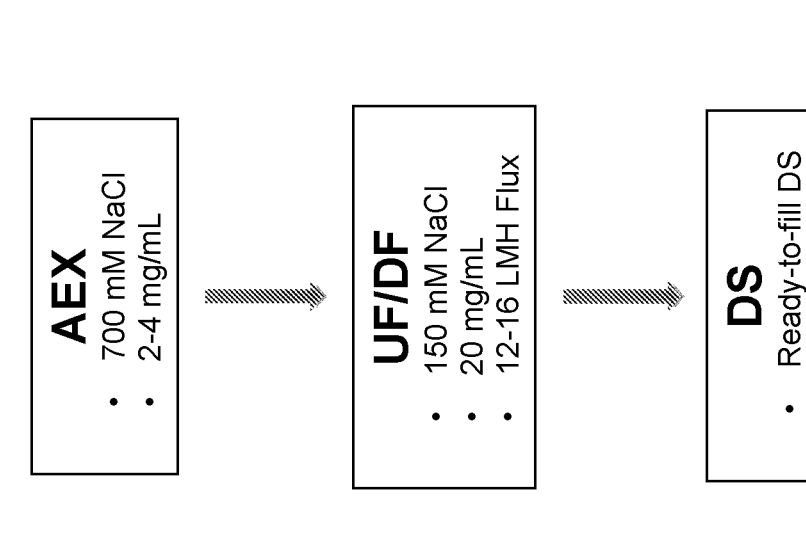
FIG. 11 illustrates a comparison between an exemplary aqueous-based platform process and an exemplary lyophilized API platform process including a ethanol precipitation step.

An aqueous-based platform process generally involves one or two chromatography separation steps, a deprotection step, and ending in an ultrafiltration/diafiltration (UF/DF) step that concentrates the oligonucleotide of interest and executes buffer exchange into a liquid formulation suitable for intrathecal (IT) administration. This platform delivers a liquid drug substance from the UF/DF operation to the parenteral fill facility for final dilution, filtration and filling. In contrast, a lyophilized API platform process often utilizes a solvent based purification process. FIG. 11 illustrates the differences between an aqueous-based platform process used to prepare a ready-to-fill liquid form of Spinraza® (nusinersen) versus a lyophilized API platform process used to prepare a lyophilized (solid) form of this product. As shown in FIG. 11, the aqueous-based platform process of Spinraza® comprises an ion exchange chromatography step followed by an ultrafiltration/diafiltration (UF/DF) step to obtain a ready-to-fill liquid form of Spinraza® (nusinersen). By contrast, the lyophilized API platform process includes an ethanol precipitation step followed by lyophilization and compounding to obtain a lyophilized (solid) form of drug product.

It would be advantageous to modify the lyophilized API platform process, currently used to prepare commercial Spinraza® (nusinersen), by replacing the ethanol precipitation step with the UF/DF step used in the aqueous-based platform process. First, for both environmental and regulatory reasons, it would be advantageous to eliminate the use of organic solvents in the final preparation of this commercial product. Second, because UF/DF can typically be used to precisely control the content of salts in the processed product, greater control of salt content could be obtained by using UF/DF instead of solvent precipitation. However, as explained below, due to the practical limitations of UF/DF and large-scale lyophilization, it has not previously been possible to successfully integrate these processes into the commercial-scale preparation of Spinraza® without including additional steps.

The difficulty of integrating UF/DF into a large-scale lyophilization occurs largely due to salt content and/or oligonucleotide content in the aqueous retentate that results from UF/DF. Whereas Spinraza® (nusinersen) is required to have a relatively low content of salts—including a sodium content of around 5% by weight in the lyophilized product—attempting to perform UF/DF with an aqueous solution having such a low salt content (and low conductivity) leads to low permeate flux through the membrane. This low permeate flux occurs, in part, due to undesirable "caking" that forms on the retentate face of the UF/DF membrane. The low permeate flux leads to both a reduction in the production rate of the desired oligonucleotide and in the concentration of the oligonucleotide in the retentate. To successfully operate the UF/DF and reach ASO concentrations ideal for lyophilization, a minimum amount of conductivity is needed in the UF/DF buffer. On the other hand, if the salt content of the UF/DF buffer is increased to a level necessary to permit a suitably high permeate flux rate (resulting in a suitably high concentration of the oligonucleotide in the retentate), then the resulting retentate contains too much salt, which will require additional step(s) to remove unwanted salts.

The methods of the present disclosure successfully overcome these difficulties by controlling salt concentration and salt content in the buffer solution. The methods integrate an aqueous purification process with a lyophilization step to create a solid API with pre-determined specifications for sodium and acetate, without adding additional steps and/or equipment. Success of the UF/DF process is determined both by operability of the UF/DF operation (flux and concentration), and the composition of the solid API after the post-UF/DF product has been processed by lyophilization. The UF/DF process was developed in which a purification process intermediate, which contains not only the target oligonucleotide but various molecular species involved in the purification process, is concentrated and processed by UF/DF such that a target sodium content is achieved post-lyophilization, and an acetate specification is met post-lyophilization. The UF/DF process of the present disclosure achieves control of the total sodium content by controlling the average number of sodium cations occupying counterion positions along the negatively charged phosphorothioate or phosphorodiester oligonucleotide backbone. The new methods also facilitate efficient operation of the UF/DF process by meeting minimum membrane permeate flux and maximum retentate concentration required for large scale manufacturing processes.

Unless otherwise defined, all technical and scientific terms used herein have the same meaning as commonly understood by persons of ordinary skill in the relevant art. In case of conflict, the present specification, including definitions, will control.

Unless stated otherwise, all percentages, parts, ratios, etc., are by weight.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure is to be limited to the specific values recited when defining a range.

The use of "a" or "an" to describe the various elements and components herein is merely for convenience and to give a general sense of the disclosure. This description should be read to include one or at least one and the singular also includes the plural unless it is clear that it is otherwise intended.

When a specified amount or value is used, it should be understood to encompass slight deviation from the specified amount or value, which one skilled in the art would understand as equivalent to or substantially the same as the specified amount or value. In some embodiments, a specified amount or value encompass±10% of the specified amount or value. In some embodiments, a specified amount or value encompass±5% of the specified amount or value.

One aspect of the present disclosure relates to methods for preparing compositions containing oligonucleotides, such as Spinraza® (nusinersen). The methods comprise subjecting an aqueous solution of the oligonucleotide to ultrafiltration/diafiltration (UF/DF) to form a retentate comprising the oligonucleotide, wherein the ultrafiltration/diafiltration (UF/DF) is carried out using an aqueous buffer solution comprising one or more salts.

In some embodiments, the one or more salts in the aqueous buffer solution may be formulated in a manner that ultimately controls the composition of the retentate. For example, in some embodiments the aqueous buffer solution may be formulated so as to control the sodium content of the retentate produced by the UF/DF—thereby indirectly controlling the sodium content of the lyophilized product. Such control is enabled by the presence of a plurality of salts in the aqueous buffer solution, including a sodium salt and a competitive salt having a different cation than sodium. Competitive salts include, for example, salts having different cations, such as ammonium, dimethylammonium, trimethylammonium, potassium, lithium, rubidium, copper, silver, or other suitable monovalent cations. The competitive salt may be a volatile salt, a non-volatile salt, or a combination thereof.

Figure 12:
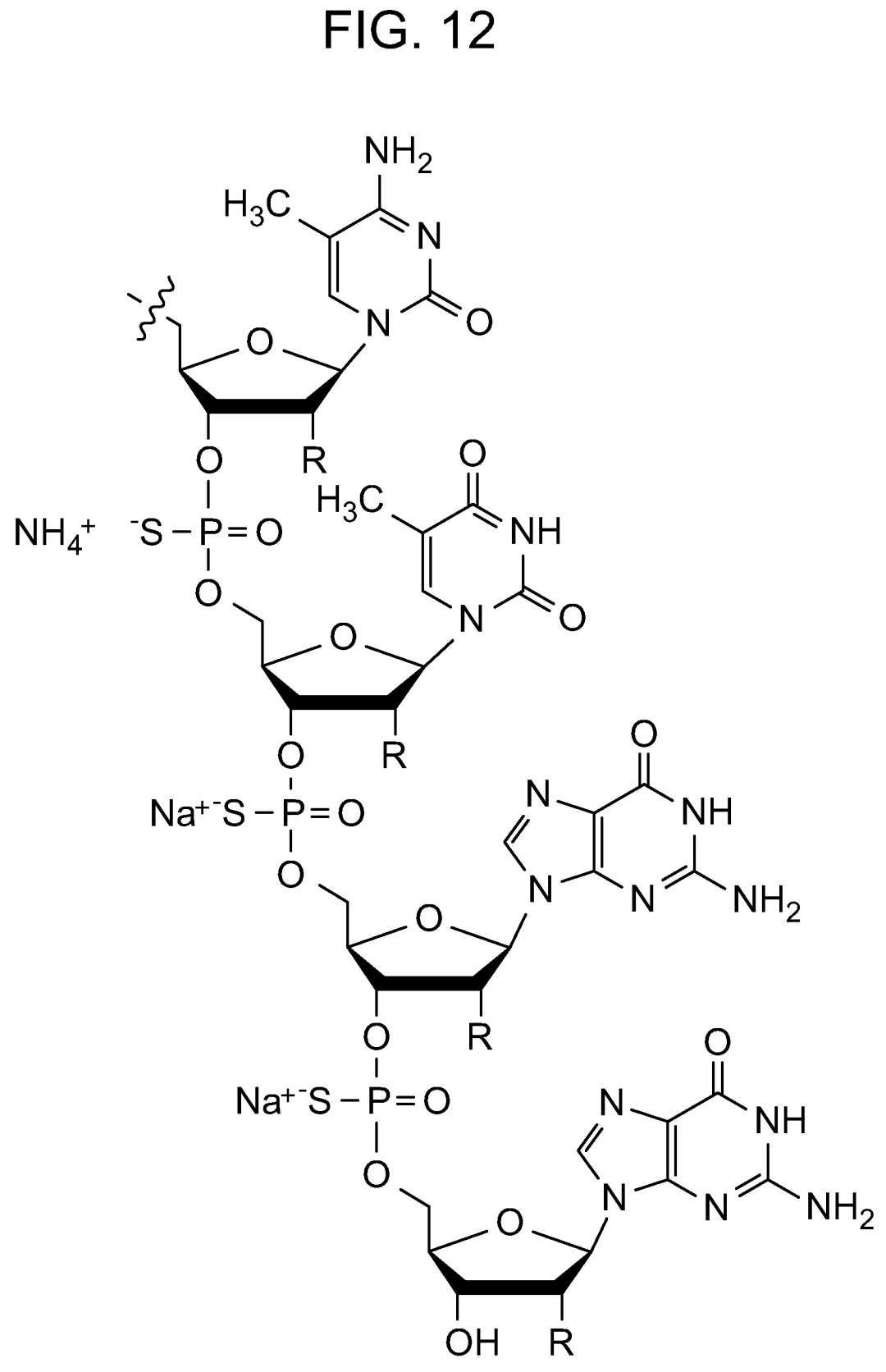

In some embodiments, the use of at least one competitive salt enables methods of the present disclosure to control the average number of sodium cations occupying the counterion positions of the oligonucleotide backbone. FIG. 12 illustrates how sodium (NO ions and ammonium (NH$_4^+$) ions may occupy different counterion positions along a negatively-charged phosphorothioate or phosphorodiester oligonucleotide backbone. Thus, in some embodiments, the present disclosure provides methods for controlling sodium content in the oligonucleotide retentate produced by the UF/DF by the introduction of one of more competitive salts in the aqueous buffer solution. In other words, the methods of present disclosure comprises subjecting an aqueous solution of the oligonucleotide to ultrafiltration/diafiltration (UF/DF) to form a retentate comprising the oligonucleotide, wherein the ultrafiltration/diafiltration (UF/DF) is carried out using an aqueous buffer solution comprising a sodium salt and a competitive salt. In some embodiments, the competitive salt is a potassium salt. In other embodiments, the competitive salt is an ammonium salt.

After buffer exchange of an aqueous solution containing both sodium cations and competitive cations occurs, the sodium and competitive cations reach an equilibrium on the counterion positions on the oligonucleotide, resulting in an oligonucleotide in solution that is not completely sodiated, i.e., oligonucleotide counterion positions are not completely occupied by sodium cations. See FIG. 12. This equilibrium ratio can be expressed as follows:

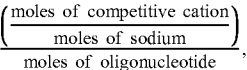

$$\left( \frac{\frac{\text{moles of competitive cation}}{\text{moles of sodium}}}{\text{moles of oligonucleotide}} \right),$$

and is controlled by the molar ratio of the competitive cation(s) to the sodium cation in the aqueous buffer solution used during the UF/DF process.

The properties of the competitive salt can affect not only the composition of the retentate following the UF/DF process, but can also affect the final composition of the solid product following lyophilization. For example, when the competitive salt is a volatile salt, it is possible to lower the total salt content of the lyophilized product (relative to the total salt content of the retentate) without affecting the sodium content.

In some embodiments, the one or more salts contained in the aqueous buffer solution may include at least one volatile salt. The UF/DF processes of the present disclosure that utilize volatile salts can achieve maximum ASO concentration in the retentate solutions with desired sodium content. The use of volatile competitive salts to lower the total salt content in the lyophilized product (relative to the total salt content of the retentate) is possible due to the acid-base properties of volatile salts. In a volatile competitive salt, the volatile competitive cation of the salt exists in equilibrium with a corresponding volatile conjugate base. The volatility of the competitive cation species (in its neutral form with the corresponding conjugate base) allows for its removal by sublimation during lyophilization.

Ammonium acetate (NH$_4$OAc) is an example of a volatile competitive salt used in some embodiments of the present disclosure. As shown below, the ammonium cation (NH$_4^+$) exists in equilibrium with ammonia (NH$_3$), while the acetate anion (AcO$^-$) exists in equilibrium with acetic acid (AcOH).

$$\text{NH}_4^+ \cdot \text{AcO}^- \rightleftharpoons \text{NH}_3 + \text{AcOH}$$

In the equilibrium shown above, the protonated ammonium cation serves as a proton source for converting the acetate anion into acetic acid, which is volatile and can be removed by lyophilization. The proton transfer from the ammonium to the acetate renders both species neutral and volatile, facilitating the removal of both species during lyophilization.

Other exemplary volatile competitive salts include, for example, ammonium salts of formic acid, propionic acid, butyric acid, lactic acid and carbonic acid.

By use of a volatile competitive salt, such as the ammonium acetate illustrated above, a subsequent lyophilization of the post-UF/DF retentate can be performed in a manner that removes significant quantities of the volatile competitive salt—while still maintaining the sodium content of the retentate. Thus, it is possible through the use of a volatile competitive salt to produce a lyophilized oligonucleotide composition having a sodium content that is controlled based on the composition of the aqueous buffer solution, while also having a total salt content that is significantly less than the total salt content of the post-UF/DF retentate. By this feature, methods of the present disclosure can produce solid, oligonucleotide APIs having a pre-determined sodium content while removing the competitive salt to trace quantities.

In some embodiments, the competitive salt may be a non-volatile salt that is not removed by lyophilization. For example, the aqueous buffer solution may include a sodium salt, such as the sodium acetate, sodium chloride, sodium bromide or sodium iodide, and a non-volatile competitive salt, such as potassium acetate, potassium chloride, potassium bromide or potassium iodide. Other non-volatile competitive salts include, for example, potassium salts, lithium salts (e.g., lithium acetate, lithium chloride, lithium bromide or lithium iodide), rubidium salts (e.g., rubidium acetate, rubidium chloride, rubidium bromide, or rubidium iodide), copper salts (e.g., copper acetate, copper chloride, copper bromide or copper iodide) and silver salts (e.g. silver acetate, silver chloride, silver bromide or silver iodide).

In the methods of the present disclosure, the composition of the aqueous buffer solution can be controlled to target a wide range of sodium content in the post-UF/DF retentate and in the post-lyophilization product—from essentially zero sodium content to sodium contents much greater than the equivalent of a fully sodiated ASO.

In some embodiments, the aqueous buffer solution comprises at least one salt selected from sodium acetate, ammonium acetate and potassium acetate. In some embodiments, the aqueous buffer solution comprises sodium acetate and ammonium acetate. In some embodiments, the aqueous buffer solution comprises sodium acetate and potassium acetate. In other embodiments, the aqueous buffer solution comprises sodium acetate, ammonium acetate and potassium acetate.

In some embodiments, the sodium content (e.g. sodium concentration) in the oligonucleotide-containing retentate is controlled by adjusting the proportion of at least one sodium salt relative to the total concentration of salts in the aqueous buffer solution. In other embodiments, the proportion of sodium cations occupying counterion positions of the oligonucleotide in the retentate is controlled by adjusting the proportion of the at least one sodium salt relative to the total concentration of salts in the aqueous buffer solution.

In some embodiments, the molar ratio of the sodium salt to the competitive salt contained in the aqueous buffer solution ranges from 1:100 to 100:1, or from 1:20 to 20:1, or from 1:10 to 10:1, or from 1:1 to 19:1, or from 5:1 to 19:1, or from 12:1 to 15:1, or from 5:1 to 10:1, or from 5:1 to 6:1, or from 5:1 to 6:1.8.

In some embodiments, the aqueous buffer solution comprises sodium acetate and ammonium acetate and the molar ratio of sodium acetate to ammonium acetate in the aqueous buffer solution ranges from 1:100 to 100:1, or from 1:20 to 20:1, or from 1:10 to 10:1, or from 1:1 to 19:1, or from 5:1 to 19:1, or from 12:1 to 15:1, or from 5:1 to 10:1, or from 5:1 to 6:1, or from 5:1 to 6:1.8. In some embodiments, the molar ratio of sodium acetate to ammonium acetate is 17:3. In some embodiments, the aqueous buffer solution comprises 34 mM of sodium acetate and 6 mM of ammonium acetate.

In some embodiments, the aqueous buffer solution comprises sodium acetate and potassium acetate and the molar ratio of sodium acetate to potassium acetate in the aqueous buffer solution ranges from 1:100 to 100:1, or from 1:20 to 20:1, or from 1:10 to 10:1, or from 1:1 to 19:1, or from 5:1 to 19:1, or from 12:1 to 15:1, or from 5:1 to 10:1, or from 5:1 to 6:1, or from 5:1 to 6:1.8. In some embodiments, the molar ratio of sodium acetate to potassium acetate is 17:3.

In some embodiments, the aqueous buffer solution comprises 34 mM of sodium acetate and 6 mM of potassium acetate.

In some embodiments, the pH of the aqueous buffer solution ranges from 4.0 to 10.0, or from 4.5 to 9.5, or from 5.0 to 9.0, or from 5.0 to 8.5, or from 5.0 to 8.0, or from 5.5 to 9.0, or from 5.5 to 8.5, or from 5.5 to 8.0, or from 5.5 to 7.5, or from 6.0 to 9.0, or from 6.0 to 8.5, or from 6.0 to 7.5, or from 6.0 to 7.0, or from 6.5 to 9.0, or from 6.5 to 8.5, or from 6.5 to 8.0, or from 6.5 to 7.5, or from 6.9 to 7.5.

In some embodiments, the aqueous buffer solution does not contain any sodium salt, such that the post-UF/DF retentate contains no sodium. In other embodiments, the aqueous buffer solution does not contain any competitive salt.

In some embodiments, methods of the present disclosure may include a step of lyophilizing the UF/DF retentate to produce lyophilized compositions comprising the target oligonucleotide. The lyophilization can remove volatile UF/DF buffer components (e.g., volatile competitive salt, such as ammonium acetate salt). The lyophilization step may be carried out as a single lyophilization, or may be carried out as a plurality of lyophilizations occurring in a single lyophilization apparatus or in multiple lyophilization apparatuses.

In some embodiments, the proportion of one or more competitive salts contained in the lyophilized composition is less than the proportion of the one or more competitive salts contained in the post-UF/DF retentate. For example, as explained above, the volatile competitive salts, such as ammonium acetate, in the aqueous buffer solution can be subsequently removed (in part or in full) during lyophilization.

Methods of the present disclosure may also include a step of adjusting the pH of the post-UF/DF retentate prior to performing a lyophilization. In some embodiments, the pH of the retentate is adjusted to a pH in the range of from 5.0 to 9.0, or from 5.0 to 8.5, or from 5.0 to 8.0, or from 5.5 to 9.0, or from 5.5 to 8.5, or from 5.5 to 8.0, or from 5.5 to 7.5, or from 6.0 to 9.0, or from 6.0 to 8.5, or from 6.0 to 7.5, or from 6.0 to 7.0, or from 6.5 to 9.0, or from 6.5 to 8.5, or from 6.5 to 8.0, or from 6.5 to 7.5. In one embodiment, the pH of retentate is adjusted to a pH in the range of 6.9 to 7.5.

The methods of the present disclosure are capable of controlling the proportion of sodium contained in lyophilized compositions with great precision. In some embodiments, the weight percentage of sodium in the lyophilized composition ranges from 0% to 100%, or from 0% to 50%, or from 1% to 25%, or from 1% to 10%, or from 2% to 10%, or from 1% to 5%, or from 5% to 10%, or from 4.3% to 6.1%, or from 4.8% to 5.4%, or from 4.9% to 5.0%, relative to the total weight of the lyophilized composition. In some embodiments, the weight percentage of sodium in the lyophilized composition is 5.2%±0.9%. In some embodiments, the oligonucleotide is nusinersen and the weight percentage of sodium in the lyophilized composition of nusinersen is 5.2%±0.9%.

For the methods of the present disclosure, the concentration of the oligonucleotide in the post-UF/DF retentate can be indirectly controlled by adjusting the total concentration of salts (and consequently the conductivity) in the aqueous buffer solution. Although performing the UF/DF using deionized water would preserve the sodium content of a fully sodiated ASO, it is not feasible to carry out UF/DF of oligonucleotides in pure water that can be directly lyophilized due to limitations of permeate flux and maximum retentate concentration. UF/DF processing of oligonucleotides in water was found to be limited by membrane surface gelling or concentration polarization phenomena, leading to reduced membrane permeate flux and creating a maximum achievable retentate concentration of only 30-40 g/L.

Figure 1:
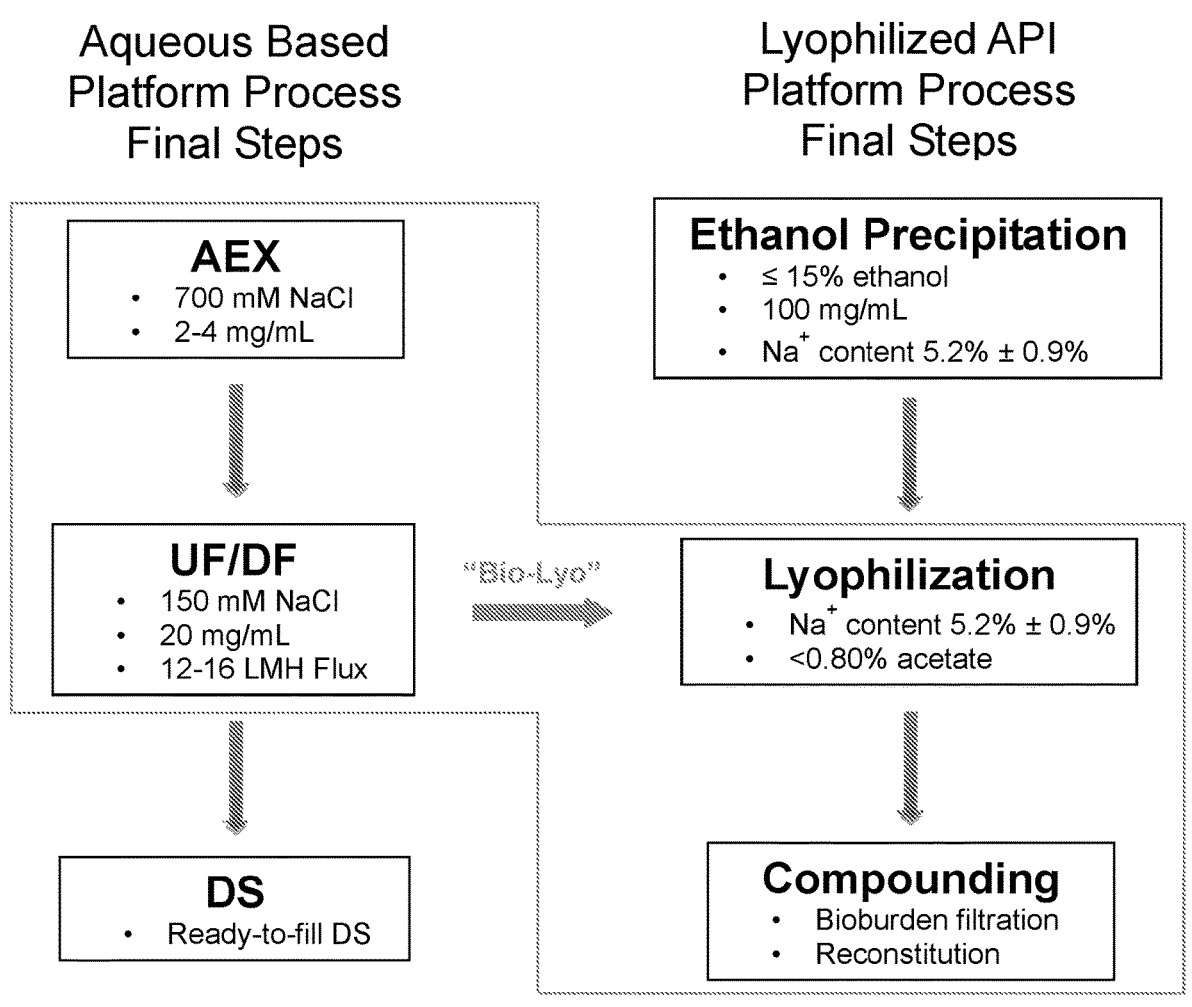
FIG. 1 depicts an exemplary integration of a solvent intensive process with an aqueous based process of the present disclosure.
Figure 2:
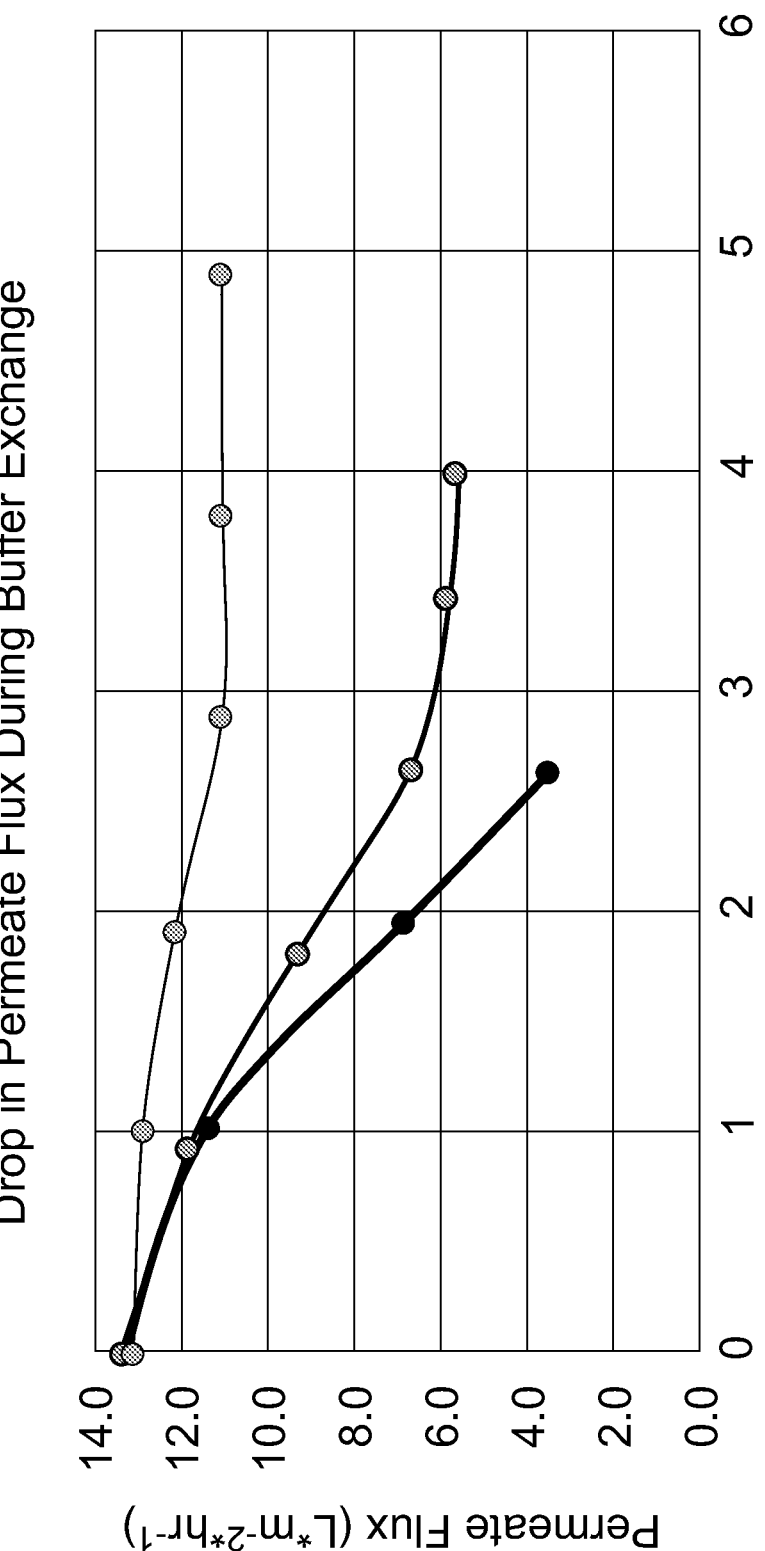
FIG. 2 is a graph illustrating permeate flux drops during buffer exchange when UF/DF is performed at different ammonium acetate concentrations.
Figure 3:
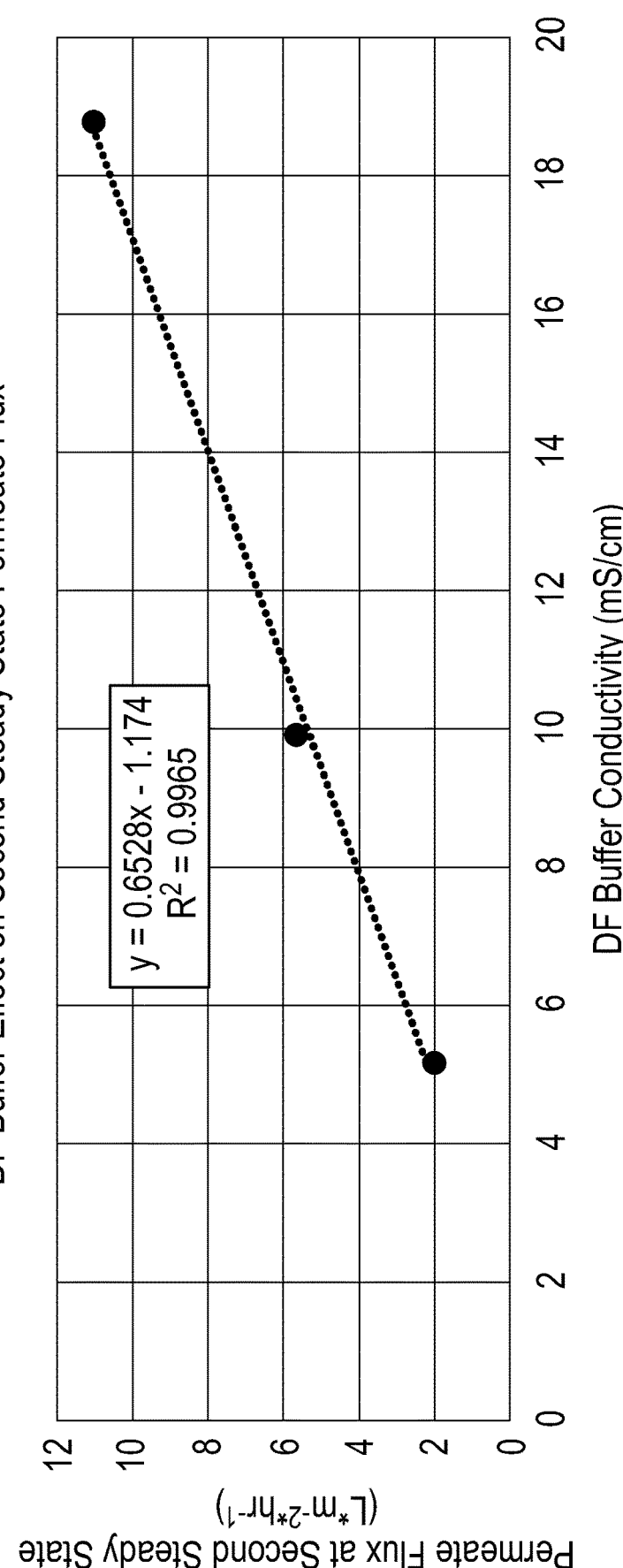
FIG. 3 is a graph illustrating the DF buffer effect on second steady state permeate flux as DF buffer conductivity is increased.

To successfully operate the UF/DF and reach ASO concentrations ideal for lyophilization (i.e., at least 50 g/L), it was discovered that a minimum amount of salt concentration (and conductivity) is needed in the UF/DF buffer. The effect of salt concentration and conductivity on permeate flux is illustrated in FIGS. 2 and 3. As shown in the study of FIG. 2, when a series of UF/DF processes were carried out using different concentrations of ammonium acetate, the permeate flux was observed to be dramatically reduced when using lower concentrations of the ammonium acetate, and the permeate flux was further reduced dramatically as the number of diavolumes of the UF/DF increased. As shown in FIG. 3, The total salt concentration is proportional to the membrane permeate flux at a given TMP.

Figure 4:
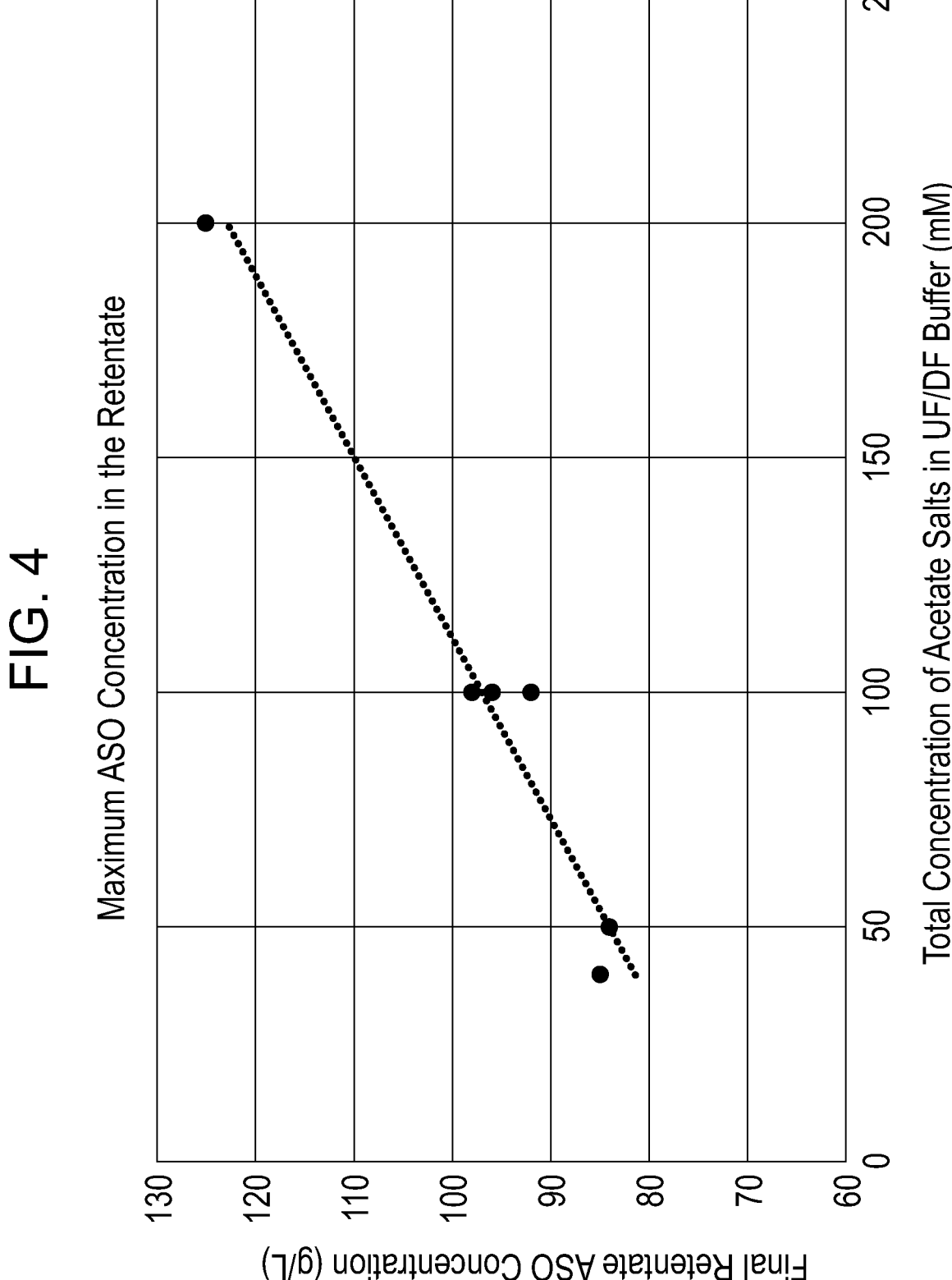
FIG. 4 is a graph illustrating maximum ASO concentration in a retentate versus total concentration of acetate salts in the UF/DF buffer.

Based on this observation, it was discovered that the total salt concentration in the aqueous buffer solution can be used to control the permeate flux of the UF/DF process and the concentration of the oligonucleotide in the post-UF/DF retentate. As illustrated in the study of FIG. 4, it was discovered that the final retentate ASO concentration can be increased by increasing the concentration of acetate salts in the aqueous buffer solution. Because an increase in the total salt concentration in the aqueous buffer solution leads to an increase in both the permeate flux and the maximum concentration of the oligonucleotide in the retentate, methods of the present disclosure can be used to achieve a desired permeate flux and a suitably-high retentate concentration to enable large-scale lyophilization without additional (i.e., solvent removal) steps.

In some embodiments, the total concentration of the one or more salts in the aqueous buffer solution ranges from 1 mM to 500 mM, or from 10 mM to 200 mM, or from 20 mM to 100 mM, or from 30 mM to 60 mM, or from 35 mM to 45 mM. In some embodiments, the total concentration of the one or more salts in the aqueous buffer solution is 40 mM.

Figure 10:
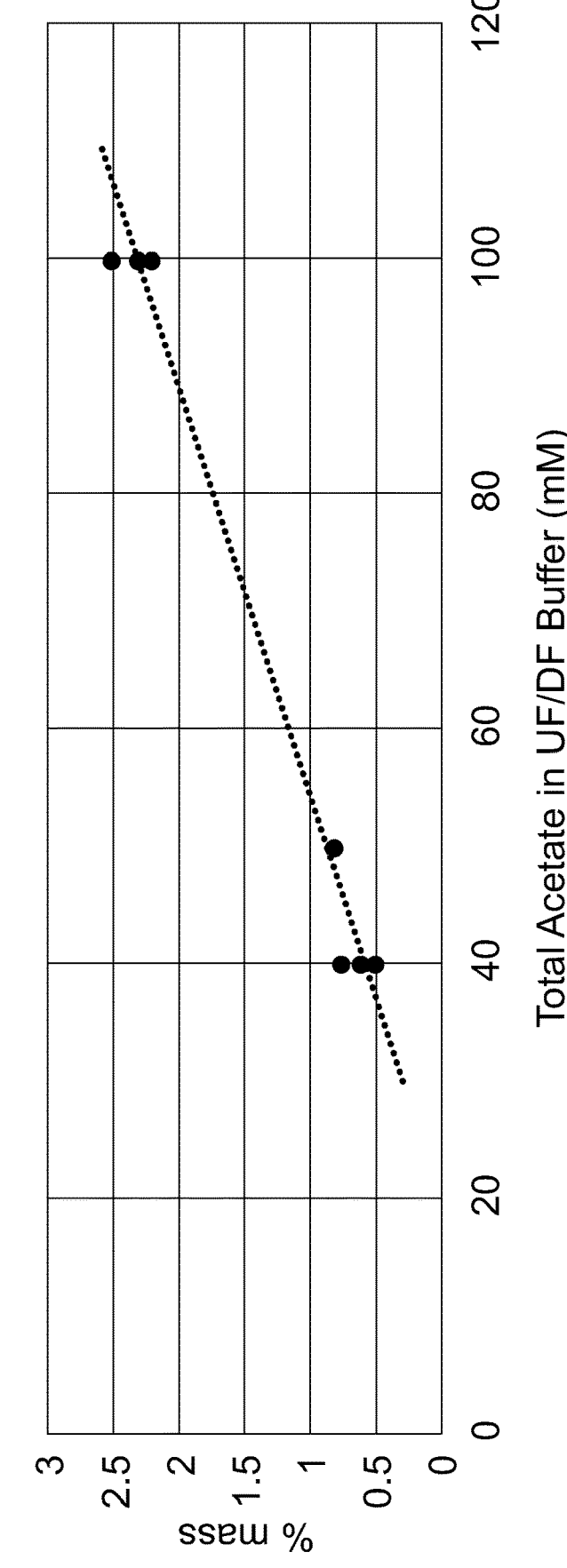
FIG. 10 is a graph illustrating the percentage (%) by mass of acetate (OAc) remaining in a solid API versus the total concentration of acetate (OAc) in the UF buffer.

When acetate salts are used as components of the aqueous buffer solution, it may be necessary to remove these salts to trace levels during the lyophilization. As illustrated in the study of FIG. 10, the acetate content in the solid API was also found to be proportional to the total salt concentration (and therefore to the total acetate concentration) in the aqueous buffer solution. Therefore, the total acetate content of the UF/DF buffer can be controlled to reduce the acetate in the solid API to trace levels. In some embodiments, the use of volatile acetate salts such as ammonium acetate can further reduce the final acetate content due to the removal of the volatile acetate salts during the lyophilization.

In some embodiments, the aqueous buffer solution comprises sodium acetate and ammonium acetate and the total concentration of sodium acetate and ammonium acetate in the aqueous buffer solution ranges from 1 mM to 500 mM, or from 10 mM to 200 mM, or from 20 mM to 100 mM, or from 30 mM to 60 mM, or from 35 mM to 45 mM. In some embodiments, the total concentration of sodium acetate and ammonium acetate in the aqueous buffer solution is 40 mM.

In other embodiments, the aqueous buffer solution comprises sodium acetate and potassium acetate and the total concentration of sodium acetate and potassium acetate ranges from 1 mM to 500 mM, or from 10 mM to 200 mM, or from 20 mM to 100 mM, or from 30 mM to 60 mM, or from 35 mM to 45 mM. In some embodiments, the total concentration of sodium acetate and potassium acetate in the aqueous buffer solution is 40 mM.

In some embodiments, the weight percentage of acetate in the lyophilized composition is less than 5%, or is less than 4%, or is less than 3%, or is less than 2%, or is less than 1%, or is less than 0.8%, or is less than 0.5%, or is less than 0.2%, relative to the total weight of the lyophilized composition. For example, in some embodiments, the weight percentage of acetate in the lyophilized composition ranges from 5% to 0.1%, or from 5% to 0.5%, or from 5% to 1%, or from 3% to 0.5%, or from 3% to 0.2%, or from 2% to 0.5%, or from 2% to 1%, or from 1% to 0.5%, or from 1% to 0.1%, or from 0.8% to 0.1%, or from 0.5% to 0.1%, or from 0.2% to 0.01%, relative to the total weight of the lyophilized composition.

The composition and properties of the aqueous buffer solution can be controlled in order to maximize the permeate flux of the UF/DF process, see FIGS. 2 and 3. Thus, the present disclosure provides methods of controlling the permeate flux of UF/DF process by adjusting the total concentration of one or more salts in the aqueous buffer solution, or by adjusting the conductivity of the aqueous buffer solution. In some embodiments, the UF/DF process is carried out with a permeate flux of at least 1 $L \cdot m^{-2} hr^{-1}$, or at least 5 $L \cdot m^{-2} hr^{-1}$, or from 5 $L \cdot m^{-2} \cdot hr^{-1}$ to 25 $L \cdot m^{-2} \cdot hr^{-1}$, or from 5 $L \cdot m^{-2} \cdot hr^{-1}$ to 20 $L \cdot m^{-2} \cdot hr^{-1}$, or from 5 $L \cdot m^{-2} \cdot hr^{-1}$ to 15 $L \cdot m^{-2} \cdot hr^{-1}$, or from 10 $L \cdot m^{-2} \cdot hr^{-1}$ to 25 $L \cdot m^{-2} \cdot hr^{-1}$, or from 8 $L \cdot m^{-2} \cdot hr^{-1}$ to 16 $L \cdot m^{-2} \cdot hr^{-1}$.

Methods of the present disclosure can also be carried out such that the UF/DF process is capable to achieving high diavolume levels, see FIG. 2. Increasing the number of diavolumes passed through the membrane during the UF/DF process, while still maintaining acceptable levels of permeate flux, enables methods of the present disclosure to maximize efficiency and productivity of the overall process. In some embodiments, the UF/DF process is carried out with a diavolume of at least 3, or at least 4, or at least 5, or from 3 to 10, or from 5 to 10, or from 5 to 8.

The methods of the present disclosure significantly increases the concentration of the oligonucleotide in the post-UF/DF retentate that enables the direct lyophilization of the post-UF/DF retentate without performing an additional water removal (i.e., concentration) step. In some embodiments, the concentration of the oligonucleotide in the retentate is at least 20 g/L, at least 30 g/L, at least 40 g/L, at least 50 g/L, or ranges from 30 g/L to 150 g/L, or ranges from 50 g/L to 150 g/L, or ranges from 60 g/L to 125 g/L, or ranges from 70 g/L to 125 g/L, or ranges from 70 g/L to 100 g/L, or from 80 g/L to 90 g/L.

The methods of the present disclosure can utilize any suitable UF/DF filter membrane known in the art. For example, in some embodiments, the UF/DF process is carried out using a membrane having a molecular weight cutoff (MWCO) from 1 kDa to 10 kDa, or from 1 kDa to 7 kDa, or from 1 kDa to 5 kDa, or from 2 kDa to 4 kDa. In some embodiments, the membrane has a MWCO of 3 kDa.

In some embodiments, the UF/DF step is carried out using tangential flow filtration.

Methods of the present disclosure may be applied to any oligonucleotide (such as an antisense oligonucleotide) having 10 to 50 nucleotides, 10 to 30 nucleotides, 10 to 25 nucleotides, 10 to 20 nucleotides, 16 to 30 nucleotides, 16 to 25 nucleotides or 16 to 20 nucleotides. In some embodiments, the oligonucleotide is nusinersen. In some embodiments, the lyophilized oligonucleotide composition is Spinraza®.

In some embodiments, methods of the present disclosure are not to limited to certain process steps, or are limited to exclude certain process steps. For example, in some embodiments, the method comprises performing at least one ultra-filtration/diafiltration (UF/DF) to obtain a retentate, and then performing at least one lyophilization of the retentate to obtain a lyophilized composition comprising the oligonucleotide. In other embodiments, the method consists of performing a single ultrafiltration/diafiltration (UF/DF) to obtain the retentate, and then performing at least one lyophilization of the retentate to obtain the lyophilized composition comprising the oligonucleotide. In still other embodiments, the method consists of performing a single ultrafiltration/diafiltration (UF/DF) to obtain the retentate, and then performing a single lyphilization of the retentate to obtain the lyophilized composition comprising the oligonucleotide.

In some embodiments, the methods of the present disclosure may be performed such that the retentate is not subjected to (i) an additional filtration, (ii) an additional buffer exchange, (iii) an additional concentration, and/or (iv) an additional purification, prior to performing the lyophilizing of the retentate to obtain the lyophilized composition. In other embodiments, methods of the present disclosure may be performed such that the retentate is not subjected to any of (i) an additional filtration, (ii) an additional buffer exchange, (iii) an additional concentration, and (iv) an additional purification, prior to performing the lyophilizing of the retentate to obtain the lyophilized composition. In some embodiments, the retentate produced from the UF/DF step is directly lyophilized without any additional steps.

Another aspect of the present disclosure relates to compositions obtained using the methods described herein. In some embodiments, the compositions comprise an oligonucleotide, such as Spinraza® (nusinersen). Compositions of the present disclosure may be in the form of aqueous solutions, such as a post-UF/DF retentate comprising an oligonucleotide, or may be in the form of a solid or semi-solid material, such as a lyophilized composition comprising an oligonucleotide.

EXEMPLIFICATION

Materials and Methods

UF/DF experiments were carried out using a KrosFlo KR2i TFF System (Spectrum Labs), and a Pellicon 3 (0.11 m², 3 kDa) regenerated cellulose membrane cassette. Laboratory-scale lyophilizations were carried out using a LyoStar 2, and manufacturing-scale lyophilizations were carried out using a LyoStar 3.

Example 1. UF/DF in Water

Figure 9:
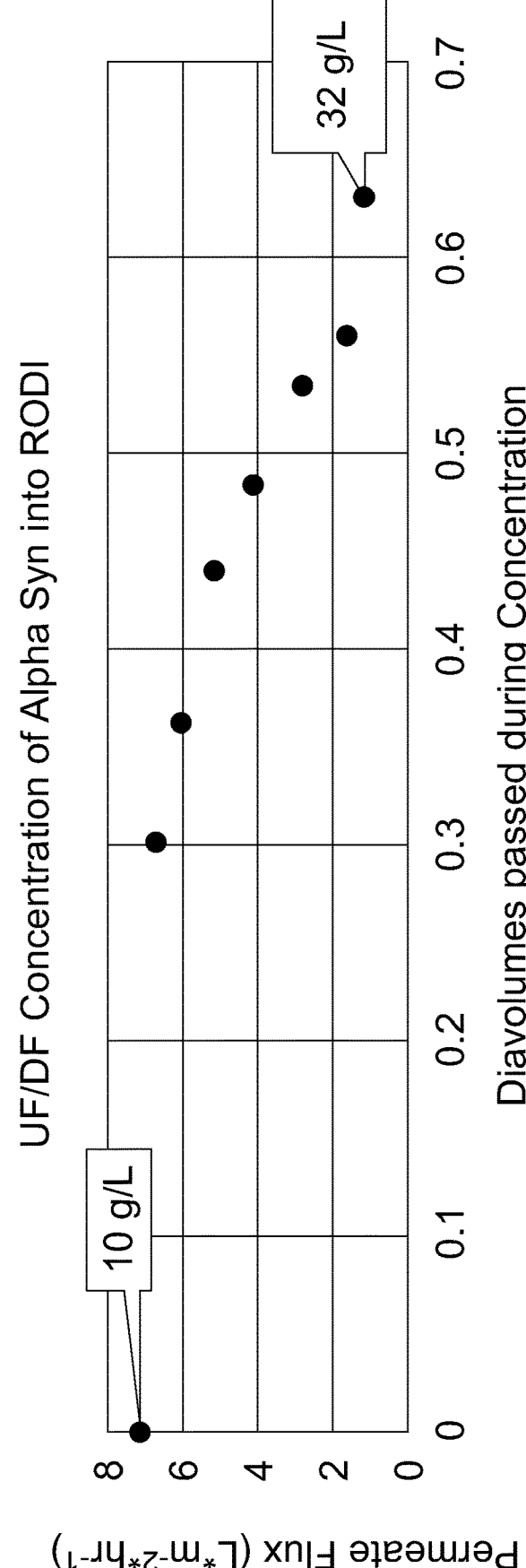
FIG. 9 is a graph illustrating how permeate flux drops as the concentration of the oligonucleotide in the retentate increases when UF/DF is carried out in water.

FIG. 9 summarizes the experimental results for a study carried out to determine how the permeate flux of a typical UF/DF process, using pure water instead of an aqueous buffer solution of the present disclosure, is affected over time as the concentration of the oligonucleotide in the retentate increases. In this study, an aqueous solution containing 10 g/L of Spinraza® (nusinersen)—labelled as "Alpha Syn" in FIG. 9—is subjected to a UF/DF process using pure water, and both the permeate flux through the membrane and the concentration of the oligonucleotide in retentate are measured over time. Concentration of the oligonucleotide was measured by spectroscopy measurements taken pre- and post-operation. Because the total mass of the ASO in the system was known, the concentrations were estimated based on the change in retained volume.

After buffer exchange of the Alpha-Syn ASO into water, an experiment was carried out to determine the maximum ASO concentration that could be achieved by concentrating the retentate using a buffer solution containing only water. The UF/DF concentration was carried out using a transmembrane pressure (TMP) of 20 psi and a crossflow of 1.5 LMM (liters/minute/meter²). The concentration step began with a retentate concentration of 10 g/L and a permeate flux of 7 LMH, and as the retentate concentration increased during the process (and the retentate volume decreased), the permeate flux dropped rapidly (FIG. 9). The permeate flux was reduced to 1 LMH at an ASO concentration in the retentate of approximately 32 g/L. This experiment demonstrated that concentration of an ASO to high concentrations (≥50 g/L) using a UF/DF buffer containing only water is not feasible.

The study in FIG. 9 indicates that UF/DF processing of oligonucleotides in water is limited by membrane surface gelling or concentration polarization phenomena, which leads to a significant reduction in membrane permeate flux and creates a maximum achievable retentate concentration between 30-40 g/L. Because a concentration of 30-40 g/L is not high enough to achieve a desirable cake structure during lyophilization, a post-UF/DF oligonucleotide in water is typically subjected to an additional unit operation for the purpose of volume reduction.

Example 2. Effects of Salt Concentration in the Aqueous Buffer Solution on the Permeate Flux The results in Example 1 demonstrated that buffer exchange into water at ideal API concentrations is not feasible, due to membrane surface gelling or concentration polarization phenomena leading to reduced membrane permeate flux. However, it was discovered that introducing salt additives into the aqueous buffer solution could increase permeate flux during the buffer exchange. Experiments attempting to buffer exchange into water showed that high conductivity correlated with high permeate flux, and that adding salt content to the diafiltration buffer was an effective way to increase permeate flux.

Ammonium acetate was chosen as an experimental additive to increase conductivity and therefore permeate flux. Both ammonium and acetate species are compatible with a lyophilized API platform process and, therefore, do not introduce any new substances to the overall manufacturing process, and both species are known to be volatile in their neutral states. Additionally, the pH of ammonium acetate is in a desirable range (6.9-7.7) based on the desired pH of an API product.

A three-experiment study was carried out to map the relationship between ammonium acetate concentration and permeate flux. The starting material for all three experiments included 105 g/L ASO, 710 mM NaCl, and 25 mM Tris, at a pH of 7.2, and all three experiments used a transmembrane pressure (TMP) of 35 psi, a crossflow of 3 LMM (liters/minute/meter²), and membrane loading of 120 g/m².

In this study, three ammonium acetate aqueous buffer solutions were prepared in which the concentration of ammonium acetate was set to 50 mM, 100 mM and 200 mM, and the resulting permeate fluxes were measured for buffer exchanges carried out on an aqueous solution of Spinraza® (nusinersen). The results (FIG. 2) show steady-state permeate flux for each condition after approximately 3 diavolumes, and a correlation between the ammonium acetate concentration and steady-state permeate flux.

As shown in FIG. 2, it was observed that the drop in permeate flux that occurs throughout the UF/DF process is directly proportional to the concentration of the ammonium acetate in the aqueous buffer solution. Using an ammonium acetate concentration of 200 mM enables the UF/DF process to maintain a permeate flux of greater than 10 $L \cdot m^{-2} \cdot hr^{-1}$ even after 5 diavolumes of the buffer have passed through the membrane. The study in FIG. 2 shows that controlling the concentration of the salts in the aqueous buffer solution can enable UF/DF methods of the present disclosure to achieve high enough concentrations of oligonucleotide in the post-UF/DF retentate that direct lyophilization of the retentate is feasible.

FIG. 3. summarizes the experimental results for a related study carried out to determine how the conductivity of the aqueous buffer solution affects the permeate flux of the UF/DF process. The relationship between buffer conductivity and permeate flux was explored to determine the minimum salt content needed for UF/DF process. In this study, three aqueous buffer solution were prepared in which the conductivity was set to about 5.1 mS/cm, about 9.8 mS/cm and about 18.9 mS/cm, and the resulting permeate fluxes were measured for buffer exchanges carried out on an aqueous solution of Spinraza® (nusinersen). Conductivity was measured using an Orion VersaStar Pro, Advanced Electrochemistry Meter.

As shown in FIG. 3, the permeate flux was found to be directly proportional to the conductivity of the aqueous buffer solution, such that the increase in permeate flux is linearly related to the increase in buffer conductivity. The results of this study demonstrate that ammonium acetate is an effective facilitator of permeate flux in a suitable ASO concentration range. A comparison of the steady-state fluxes (FIG. 2) and the buffer conductivity (FIG. 3) in this study indicated a linear relationship and, therefore, an ability to target a specific flux (FIG. 3), which is critical to controlling the UF/DF operation.

Example 3. Correlation Between the Total Concentration of Salts in the Aqueous Buffer and Maximum Oligonucleotide Concentration in Retentate FIG. 4 summarizes the experimental results for a study carried out to determine how the total concentration of salts in the aqueous buffer solution affects the final concentration of the oligonucleotide in the post-UF/DF retentate. In this study, a number of aqueous buffer solutions (200 mM ammonium acetate; 50 mM ammonium acetate and 50 mM sodium acetate; 75 mM ammonium acetate and 25 mM sodium acetate; 90 mM ammonium acetate and 10 mM sodium acetate; 7.5 mM ammonium acetate and 42.5 mM sodium acetate; 4 mM ammonium acetate and 36 mM sodium acetate) were prepared in which the total concentration of acetate salts was increased from about 4 mM to about 200 mM, and the resulting post-UF/DF retentate concentrations were measured for buffer exchanges carried out to 8 diavolumes on an aqueous solution of Spinraza® (nusinersen). Following the UF/DF to 8 diavolumes, a final concentration step was performed to reduce retentate volume until permeate flux dropped to <2 LMH.

As shown in FIG. 4, it was observed that the concentration of the oligonucleotide in the post-UF/DF retentate is directly proportional to the total concentration of acetate salts in the aqueous buffer solution. While increasing UF/DF buffer conductivity (total salt concentration) facilitated higher permeate flux, it also facilitated higher maximum achievable retentate concentration. This relationship was also linear, demonstrating the ability to target a maximum achievable retentate concentration by manipulation of UF/DF buffer salt concentration, The study in FIG. 4 surprisingly shows that controlling the concentration of salts in the aqueous buffer solution can also control the concentration of the oligonucleotide in the retentate—enabling the UF/DF process to be carried out in a manner that significantly increases the retentate concentration, thereby allowing direct lyophilization of the retentate (without additional steps) to form solid APIs.

The studies shown in FIGS. 2 and 4 show that the maximum achievable ASO concentration in the retentate is directly proportional to both the total acetate concentration in the UF/DF buffer and the permeate flux. A minimum concentration of 80 g/L was targeted to ensure acceptable quality and density of the solid cake, as well as to fit into an existing lyophilizer (LyoStar3).

Total salt concentration of the buffer controls permeate flux and maximum ASO concentration in the retentate that can be achieved, whereby an increase in total salt results in a reproducible increase in flux and maximum retentate concentration. By this method of control, one can target and reproducibly achieve a desired permeate flux and maximum retentate concentration.

Example 4. Methods of Controlling Sodium Content in the Post-Lyophilized Oligonucleotide Composition FIG. 5 and Table 1 summarize the experimental results for a study carried out to determine how the molar ratio of sodium and ammonium acetate salts in the aqueous buffer solution affects the amounts of sodium and ammonium in the post-lyophilized compositions. UF/DF experiments in this study all used the following conditions:

TMP of 35 psi

Crossflow of 3 LMM

Membrane loading between 50-275 $g/m^2$.

Lyophilization of the UF/DF pools was carried out in LyoGuard trays, using the following conditions:

Initial freezing temperature of −50° C.

Primary drying at 23° C. and 100 mTorr

Secondary drying at 30° C. and 100 mTorr.

In this study, a series of aqueous buffer solutions (see Table 1) were prepared in which the contents of sodium acetate (NaOAc) and ammonium acetate ($NH_4OAc$) were varied such that the molar ratio of sodium to ammonium increased from 0% to 100%, and mass percentages of sodium and ammonium in the post-lyophilized compositions were measured.

Figure 5:
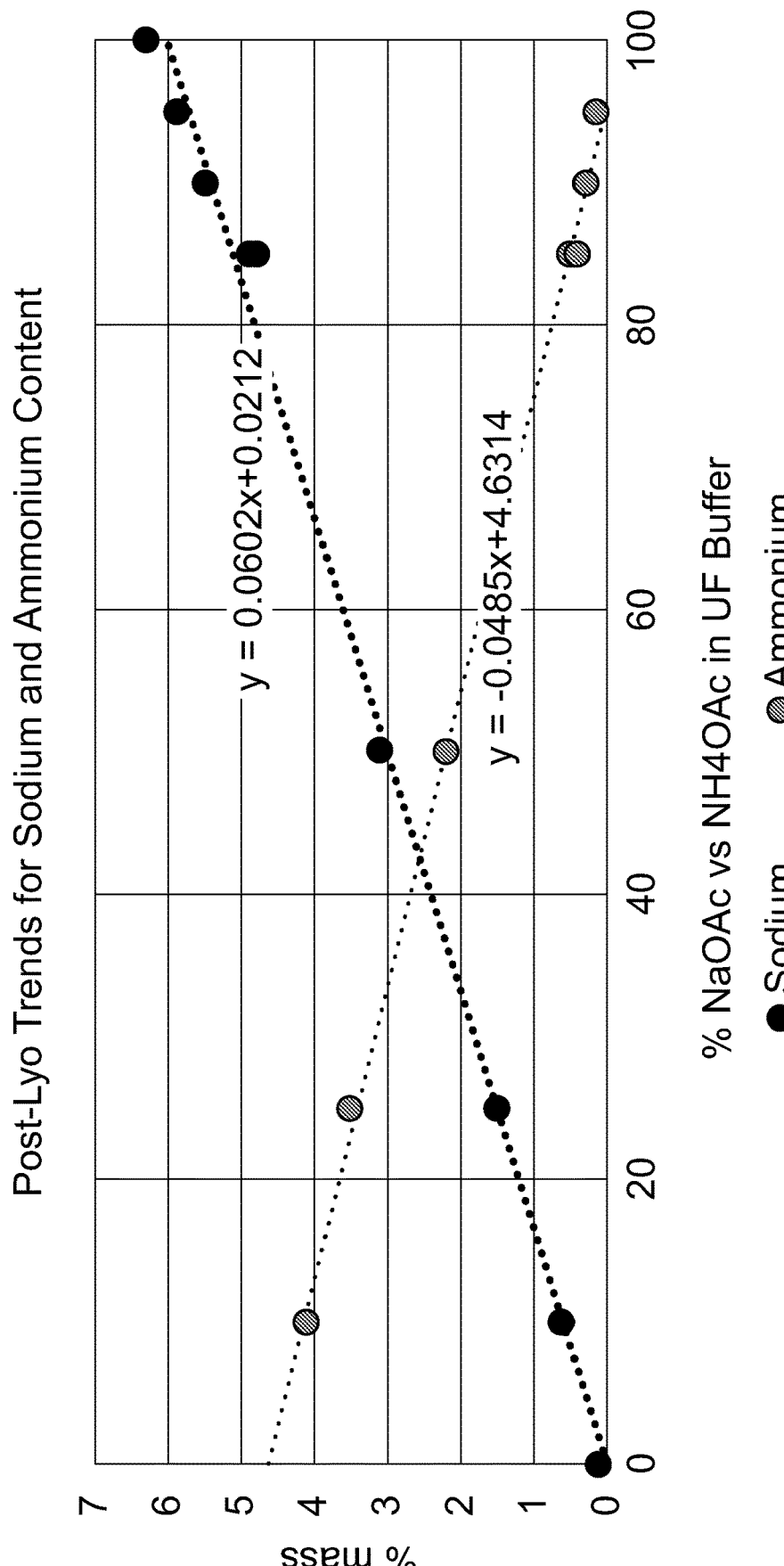
FIG. 5 is a graph illustrating post lyophilization (post-lyo) trends for sodium and ammonium content.

Samples of the post-lyophilized solid APIs were analyzed for sodium (using inductively-coupled plasma optical emission spectrum (ICP-OES)), ammonia (using the $NH_3$ Bio Test Kit for the Cedex BioHT Analyzer) and acetate content (using the LC-UV method (comparison to a standard)) (FIG. 5). The target mass % for sodium was 5.2±0.9%, and the target for acetate was ≤0.8 mass %. No specification on ammonia existed, but it was desired to reduce the amount of residual ammonia as much as possible, or to completely eliminate it from the API. An intermediate ammonia target of 0.5% was chosen, as it appeared to be the lowest consistently achievable level under the tested conditions.

TABLE 1

| Ex. | Buffer (NaOAc/ NH4OAc) Ratio | Buffer % NaOAc | Buffer Total Acetate Content (mM) | Post-Lyo Na content (% mass) | Post-Lyo NH4 content (% mass) | Post-Lyo Acetate content (% mass) |
|---|---|---|---|---|---|---|
| 1 | 200 mM NH4OAc | 0 | — | 0.1 | — | NT |
| 2 | 10 mM NaOAc, 90 mM NH4OAc | 10 | 100 | 0.6 | 4.1 | 2.3 |
| 3 | 25 mM NaOAc, 75 mM NH4OAc | 25 | 100 | 1.5 | 3.5 | 2.5 |
| 4 | 50 mM NaOAc, 50 mM NH4OAc | 50 | 100 | 3.1 | 2.2 | 2.2 |
| 5 | 42.5 mM NaOAc, 7.5 mM NH4OAc | 85 | 50 | 4.8 | 0.5 | 0.8 |
| 6 | 34 mM NaOAc, 6 mM NH4OAc | 85 | 40 | 4.9 | 0.4 | 0.5 |
| 7 | 36 mM NaOAc, 4 mM NH4OAc | 90 | 40 | 5.5 | 0.25 | 0.742 |
| 8 | 38 mM NaOAc, 2 mM NH4OAc | 95 | 40 | 5.9 | 0.14 | 0.597 |
| 9 | 40 mM NaOAc | 100 | 40 | 6.3 | NT | NT |

The tradeoff between sodium and ammonia was consistent throughout the range of sodium to ammonium ratios in the buffer systems tested (FIG. 5), demonstrating the ability to target specific concentrations of sodium and ammonium in the final product (solid API). In all of the examples in FIG. 5, the UF/DF retentates were concentrated to similar concentrations of 80-85 g/L. Because the sodium present in solution in the UF/DF pool was not removed by lyophilization, the final API sodium values include the sodium present in the buffer carried into the lyophilization process. If the UF/DF pool were at a lower concentration of ASO (larger volume), the sodium values would be shifted higher and, conversely, if the UF/DF pool could be increased to a higher concentration (smaller volume), the sodium values would be shifted lower. Any change in final UF/DF retentate ASO concentration must be considered when targeting a specific sodium and ammonia content.

As shown in FIG. 5, it was found that the ratio of ammonium to sodium in the UF/DF buffer determines the final content of sodium and ammonium in the post-lyophilized composition. Lyophilization of the UF/DF pools was carried out in LyoGuard trays, using primary drying conditions of 23° C. and 100 mTorr, and secondary drying conditions of 30° C. and 100 mTorr. Under the lyophilization conditions of this study, the final content of sodium and ammonium were observed to be linearly related to the respective molar ratios of the sodium acetate and the ammonium acetate.

Figure 6:
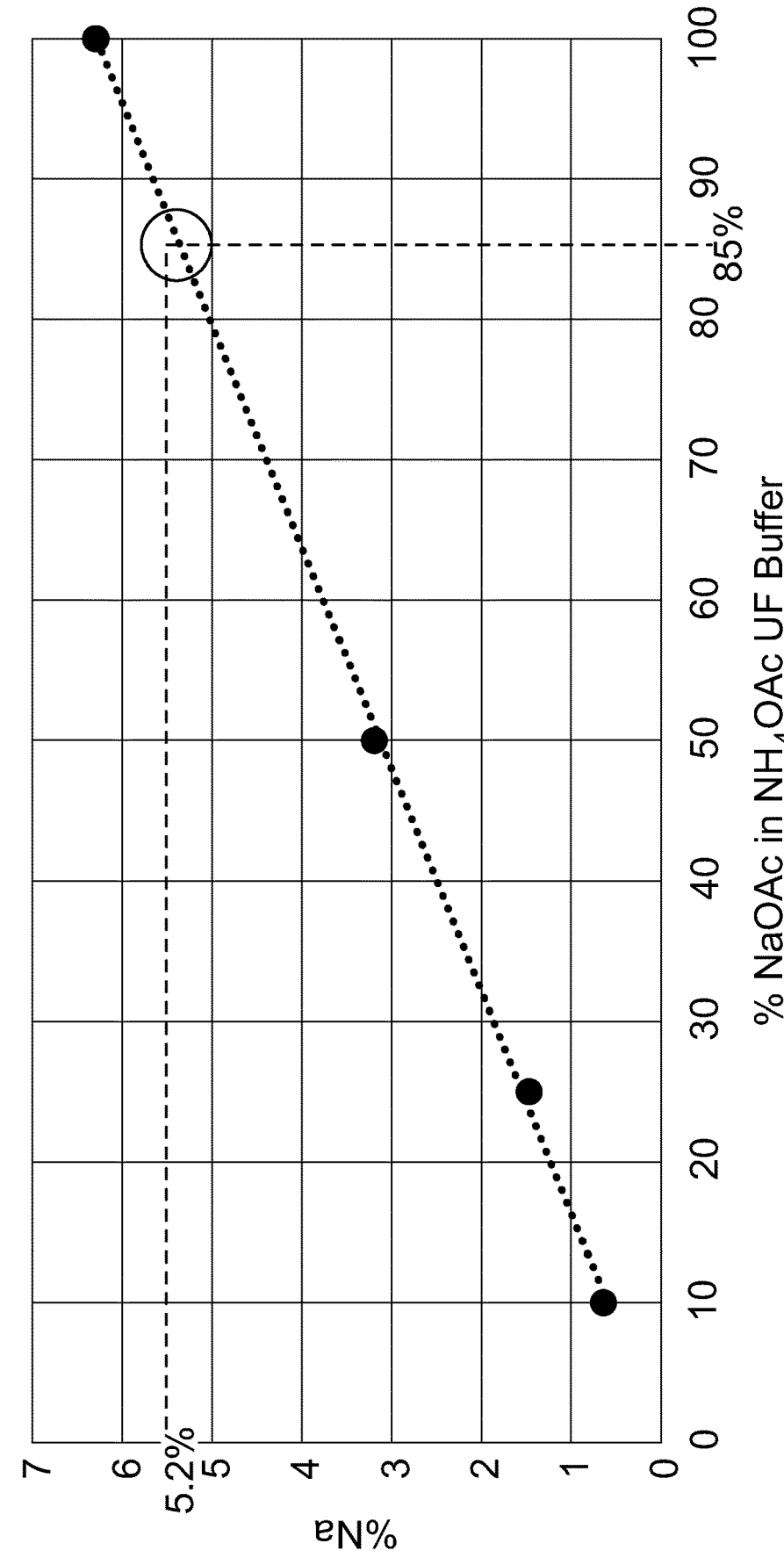
FIG. 6 is a graph illustrating the sodium (Na) content in the post UF/DF retentate versus the percentage (%) of sodium acetate (NaOAc) in UF buffers containing different amount ammonium acetate (NH₄OAc).

As illustrated in the related study summarized in FIG. 6, fine-tuning of the UF/DF buffer component ratios (e.g., the ratio of ammonium to sodium) can control the post-lyophilization sodium content, allowing the solid API to meet certain specifications such as the critical sodium content of 5.2%±0.9%. The sodium content results from this study were lower than the target of 5.2±0.9 mass %, but the linear trend allows for prediction of the necessary UF/DF buffer compositions (of sodium acetate and ammonium acetate) that would result in sodium contents within the target range. As shown in FIG. 6, extrapolating the data to the center of the target sodium content range predicted that operating the UF/DF with a buffer consisting of 85% sodium acetate and 15% ammonium acetate would result in a product sodium content of approximately 5.2 mass %.

Example 5. Correlation of Acetate Content in the Post-Lyophilized Oligonucleotide Composition with the Total Acetate Content in the Aqueous Buffer FIG. 10 summarizes the experimental results for a study carried out to determine how the total acetate content in the aqueous buffer solution affects the amount of acetate in the post-lyophilized solid API. In this study, a series of aqueous buffer solutions were prepared in which the total acetate concentrations were varied from 40 mM to 100 mM (see Ex. 2-8 in Table 1), and the mass percentage of acetate in the post-lyophilized compositions were measured. As shown in FIG. 10, the residual acetate content in the post-lyo API was found to be proportional to the total content of acetate salts in the UF/DF buffer. A linear trend was observed between the total acetate content in the UF/DF buffer matrix and the residual acetate content in the solid API. The buffer conditions that met the acetate specification of ≤0.8 mass % all contained 40 mM total acetate.

The residual acetate content was also not found to be influenced by the ammonium/sodium cation ratio. Furthermore, based on the volatility of ammonium acetate under lyophilization conditions, reduction of the total acetate salt concentration in the aqueous buffer solution allowed for removal of acetate to trace levels post-lyophilization.

Based in part on the experimental studies described above, it was discovered that optimization of the ratio of sodium acetate to ammonium acetate in the UF/DF buffer, along with reduction of the total acetate salt concentration, can successfully link an aqueous downstream process including UF/DF to a lyophilized API.

Example 6. Large Scale Preparation of Lyophilized API

Large-scale experiments were carried out using a fixed molar ratio of the sodium salt in the aqueous buffer solution, and the concentration of the oligonucleotide in the post-UF/DF retentate (labelled as "Pre-Lyo Oligo. Conc" in Table 2 below) and the moisture content, sodium content and acetate content of the post-lyophilization composition were measured. In these experiments, the oligonucleotide Spinraza® (nusinersen) was subjected to UF/DF methods of the present disclosure at the fixed molar ratio of the sodium salt.

Based on the previous experimentation, 6 mM ammonium acetate, 34 mM sodium acetate (85% sodium acetate to 15% ammonium acetate, with a total acetate concentration of 40 mM) was chosen as the buffer matrix that would best target the endpoints for maximum ASO concentration in the retentate, sodium content, and acetate content. The conditions were confirmed at lab scale, then repeated at manufacturing (MFG) scale (18 mmol). The UF/DF pool from the manufacturing process was split, with a portion lyophilized at lab scale (labelled as "Lab Scale Lyo" in Table 2), and the remaining portion lyophilized at the manufacturing scale.

As illustrated in Table 2, no significant differences were observed for sodium and acetate post-lyophilization, demonstrating that cation control by manipulation of the UF/DF buffer is scalable. The maximum achievable UF/DF pool concentrations were the same at both scales. The water content in the solid API was observed to be slightly higher at manufacturing scale, which was a result of equipment differences. Overall, scale up of the cation and acetate control by manipulation of UF/DF buffer, and facilitation of permeate flux and retentate concentration by salt composition were successful, demonstrating the scalability of the process.

TABLE 2

| | | Pre-Lyo ASO. Conc. in Retentate (g/L) | Post-Lyo Moisture (%) | Post-Lyo Sodium (%) | Post-Lyo Acetate (%) |
|---|---|---|---|---|---|
| Ex. | UF/DF matrix | | | | |
| Final UF/DF buffer conditions and results, at lab and manufacturing scales | | | | | |
| 10 | 6/34 (NH₄OAc/NaOAc) Lab Scale UF/DF and Lyo | 85 | 1.0 | 4.9 | 0.4 |
| 11 | Eng run 6/34 (NH₄OAc/NaOAc) MFG scale UF/DF, Lab Scale Lyo | 85 | 1.1 | 4.9 | 0.5 |
| 12 | Eng run 6/34 (NH₄OAc/NaOAc) MFG scale UF/DF and Lyo | 85 | 2.8 | 4.9 | 0.5 |

Figure 7:
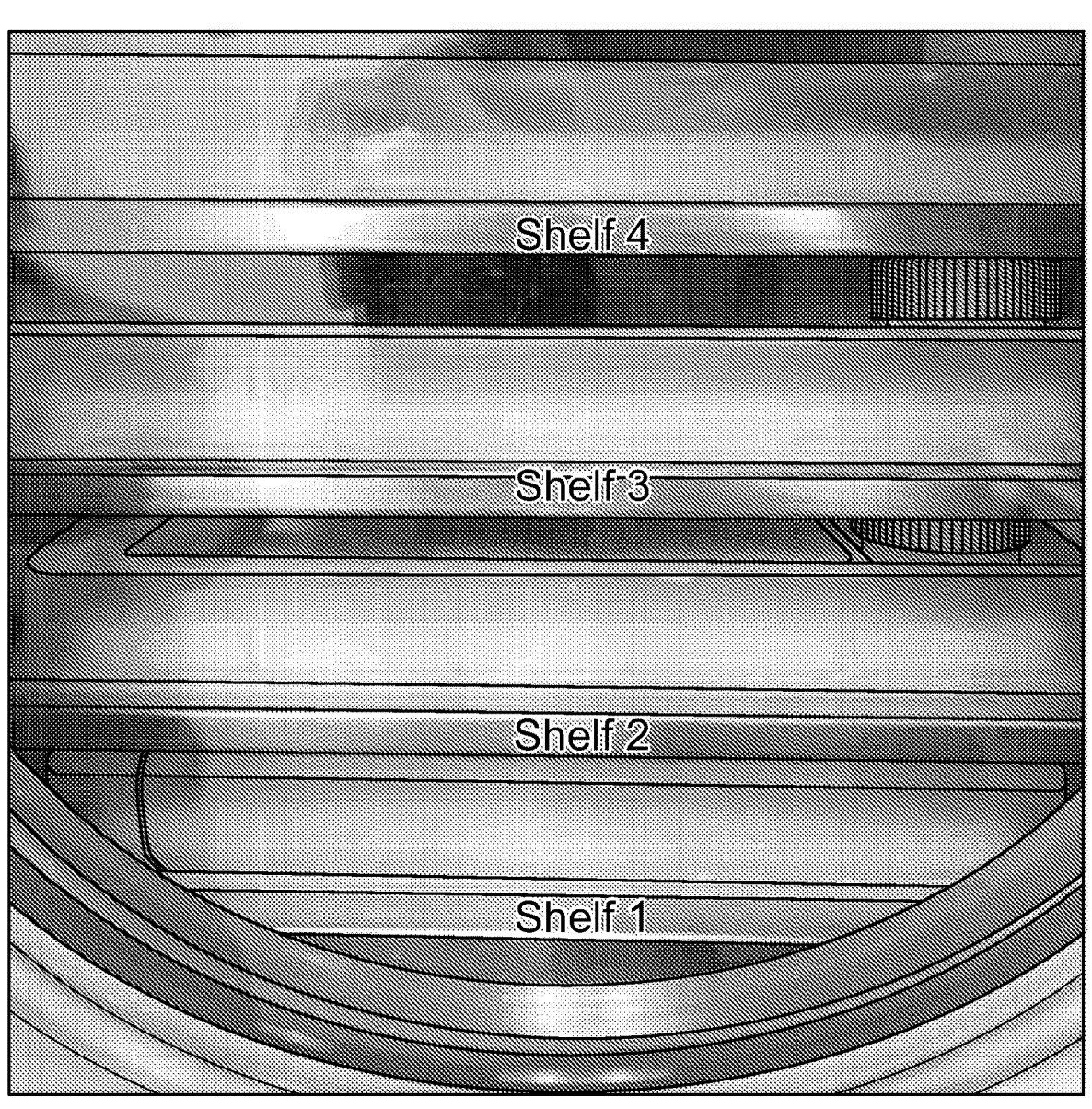
FIG. 7 is a picture of an exemplary lyophilizer chamber with LyoGuard trays.
Figure 8:
FIG. 8 is a picture of an exemplary lyophilized ASO material in the tray and bag.
Figure 8:
Figure 8:
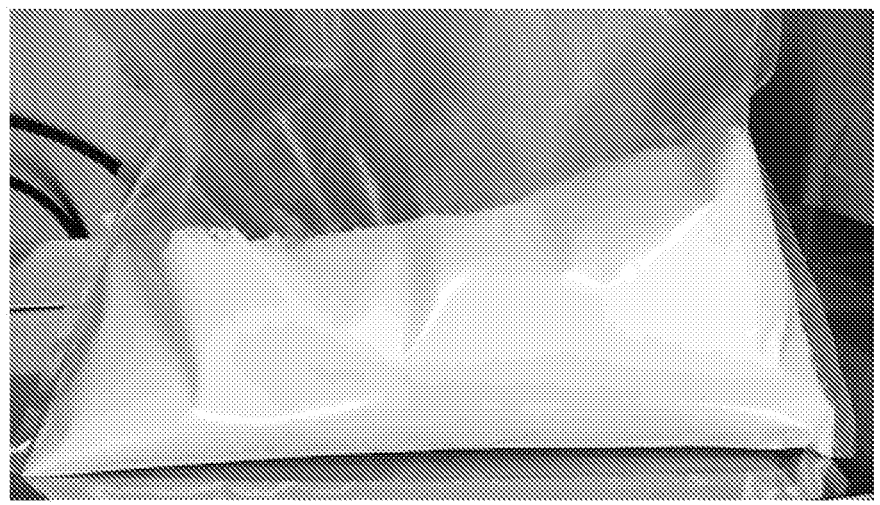

Bulk lyophilization was performed on materials obtained from manufacturing scale run (Ex. 12 in Table 2) using 4 LyoGuard trays for a total liquid volume of 6 L. FIG. 7 shows the 4 LyoGuard trays containing the lyophilized material. The lyophilization process was modified to promote maximum removal of volatile UF/DF buffer components. This bulk lyophilization process involved −50° C. freezing, 23° C. primary drying followed by 30° C. secondary drying at 150 mTorr pressure. Moisture content and volatile buffer components were successfully removed to trace amounts, meeting the API specifications. FIG. 8 shows the lyophilzed material in a LyoGuard tray and subsequently transferred to a storage bag.

The final buffer chosen was 34 mM NaOAc and 6 mM NH₄OAc, and the conditions and results for the engineering run (Ex. 12 in Table 2) are summarized below:

Solid API Na Content: 4.9-5.0% (Target 5.2%±0.9%)

Post-UF/DF Concentration: Allowed for 85 g/L liquid API

Permeate Flux: Maintained>10 LMH Flux

Duration of UF/DF Process: Unit operation complete in 1 day

Final Acetate Content: Lowest residual acetate post-lyo

Stability of Post-Lyo Composition: Solid API Stable at 25° C. for 31 days

While various embodiments of the present disclosure have been shown and described herein, it will be obvious that such embodiments are provided by way of example only. Numerous variations, changes and substitutions may be made without departing from the disclosure herein. Accordingly, it is intended that the disclosure be limited only by the spirit and scope of the appended claims.

The invention claimed is:

1. A method for preparing a composition comprising an oligonucleotide, the method comprising subjecting an aqueous solution of the oligonucleotide to ultrafiltration/diafiltration (UF/DF) to form a retentate comprising the oligonucleotide, wherein the ultrafiltration/diafiltration (UF/DF) is carried out using an aqueous buffer solution and wherein the aqueous buffer solution comprises i) sodium acetate and ammonium acetate or ii) sodium acetate and potassium acetate.

2. The method of claim 1, wherein the total concentration of sodium acetate and ammonium acetate or the total concentration of sodium acetate and potassium acetate in the buffer solution is in the range of 10 mM to 200 mM.

3. The method of claim 2, wherein the total concentration of sodium acetate and ammonium acetate or the total concentration of sodium acetate and potassium acetate in the buffer solution is 40 mM.

4. The method of claim 1, wherein
the aqueous buffer solution comprises sodium acetate and ammonium acetate, and the total concentration of sodium acetate and ammonium acetate ranges from 20 mM to 100 mM; or
the aqueous buffer solution comprises sodium acetate and potassium acetate, and the total concentration of sodium acetate and potassium acetate ranges from 20 mM to 100 mM.

5. The method of claim 1, wherein the molar ratio of sodium acetate to ammonium acetate or the molar ratio of sodium acetate to potassium acetate in the buffer solution ranges from 1:20 to 20:1.

6. The method of claim 5, wherein:
the aqueous buffer solution comprises sodium acetate and ammonium acetate, and the molar ratio of sodium acetate to ammonium acetate in the aqueous buffer solution is 17:3; or
the aqueous buffer solution comprises sodium acetate and potassium acetate, and the molar ratio of sodium acetate to potassium acetate in the aqueous buffer solution is 17:3.

7. The method of claim 1, wherein the aqueous buffer solution comprises 34 mM of sodium acetate and 6 mM of ammonium acetate or the aqueous buffer solution comprises 34 mM of sodium acetate and 6 mM of potassium acetate.

8. The method of claim 1, wherein the ultrafiltration/diafiltration (UF/DF) is carried out with a permeate flux ranges from 5 $L \cdot m^{-2} \cdot hr^{-1}$ to 25 $L \cdot m^{-2} \cdot hr^{-1}$.

9. The method of claim 1, wherein
the ultrafiltration/diafiltration (UF/DF) is carried out with a diavolume from 3 to 10.

10. The method of claim 1, wherein the concentration of the oligonucleotide in the retentate is from 30 g/L to 150 g/L.

11. The method of claim 1, further comprising subjecting the retentate to lyophilization to form a lyophilized composition comprising the oligonucleotide.

12. The method of claim 11, wherein
i) the weight percentage of sodium in the lyophilized composition ranges from 2% to 10%.

13. The method of claim 11, wherein the weight percentage of acetate in the lyophilized composition is less than 3%.

14. The method of claim 1, wherein the oligonucleotide is an antisense oligonucleotide having 16 to 30 nucleotides.

15. The method of claim 1, wherein the oligonucleotide is nusinersen.

16. The method of claim 1, wherein the aqueous buffer solution comprises sodium acetate and ammonium acetate, and the total concentration of sodium acetate and ammonium acetate ranges from 30 mM to 60 mM; or the aqueous buffer solution comprises sodium acetate and potassium acetate, and the total concentration of sodium acetate and potassium acetate ranges from 30 mM to 60 mM.

17. The method of claim 1, wherein the molar ratio of sodium acetate to ammonium acetate or the molar ratio of sodium acetate to potassium acetate in the buffer solution ranges from 1:1 to 19:1.

18. The method of claim 1, wherein the molar ratio of sodium acetate to ammonium acetate or the molar ratio of sodium acetate to potassium acetate in the buffer solution ranges from 5:1 to 19:1.

19. The method of claim 1, wherein the concentration of the oligonucleotide in the retentate is from 70 g/L to 125 g/L.

20. The method of claim 1, wherein the ultrafiltration/diafiltration (UF/DF) is carried out using a membrane having a molecular weight cutoff (MWCO) in the range from 1 kDa to 7 kDa.

21. The method of claim 1, the ultrafiltration/diafiltration (UF/DF) is carried out by a tangential flow filtration.

22. The method of claim 11, wherein the weight percentage of the sodium in the lyophilized composition is 5.2%±0.9%.

\* \* \* \* \*